United States Patent
Magnani et al.

(10) Patent No.: US 9,629,933 B2
(45) Date of Patent: Apr. 25, 2017

(54) DELIVERY OF CONTRASTING AGENTS FOR MAGNETIC RESONANCE IMAGING

(75) Inventors: Mauro Magnani, Urbino (IT); Antonella Antonelli, Urbino (IT)

(73) Assignee: Erydel S.P.A. (IT)

( * ) Notice: Subject to any disclaimer, the term of this patent is extended or adjusted under 35 U.S.C. 154(b) by 1339 days.

(21) Appl. No.: 12/306,892

(22) PCT Filed: Jul. 3, 2007

(86) PCT No.: PCT/EP2007/006349
§ 371 (c)(1),
(2), (4) Date: Nov. 4, 2009

(87) PCT Pub. No.: WO2008/003524
PCT Pub. Date: Jan. 10, 2008

(65) Prior Publication Data
US 2010/0061937 A1    Mar. 11, 2010

(30) Foreign Application Priority Data
Jul. 3, 2006 (GB) .................................. 0613183.3

(51) Int. Cl.
*A61K 49/18* (2006.01)

(52) U.S. Cl.
CPC ....... *A61K 49/1896* (2013.01); *Y10S 977/773* (2013.01); *Y10S 977/93* (2013.01)

(58) Field of Classification Search
None
See application file for complete search history.

(56) References Cited

U.S. PATENT DOCUMENTS

| | | | |
|---|---|---|---|
| 4,669,481 A | 6/1987 | Eisenberg et al. | |
| 5,492,814 A * | 2/1996 | Weissleder | 435/7.25 |
| 5,928,958 A | 7/1999 | Pilgrimm | |
| 6,139,836 A | 10/2000 | Magnani et al. | |
| 6,368,574 B1 * | 4/2002 | Akeson et al. | 424/9.32 |
| 6,933,331 B2 | 8/2005 | Yadav et al. | |
| 2003/0028071 A1* | 2/2003 | Handy et al. | 600/12 |
| 2003/0092029 A1* | 5/2003 | Josephson et al. | 435/6 |
| 2004/0076586 A1 | 4/2004 | Koening et al. | |
| 2005/0261575 A1 | 11/2005 | Conolly et al. | |
| 2006/0078502 A1 | 4/2006 | Dewanjee | |
| 2006/0099719 A1* | 5/2006 | Curcio | G01N 33/558 436/514 |
| 2006/0270030 A1* | 11/2006 | Voigt et al. | 435/325 |

FOREIGN PATENT DOCUMENTS

| | | |
|---|---|---|
| WO | WO 91/16080 | 10/1991 |
| WO | WO 02/22011 | 3/2002 |
| WO | WO 2006/012201 | 2/2006 |

(Continued)

OTHER PUBLICATIONS

Machine Translation of WO 2006048321 A1. 10 pages.*

(Continued)

*Primary Examiner* — Isaac Shomer
(74) *Attorney, Agent, or Firm* — Foley & Lardner LLP

(57) ABSTRACT

Erythrocytes exposed to dialysis with an hypotonic buffer stably take up superparamagnetic iron oxide nanoparticles and may be used MRI contrast agents. Such erythrocytes may also be used as drug delivery vehicles.

20 Claims, 3 Drawing Sheets

(56) References Cited

FOREIGN PATENT DOCUMENTS

| WO | WO 2006/048321 | | 5/2006 |
|----|----|----|----|
| WO | WO 2006048321 | A1 * | 5/2006 |

OTHER PUBLICATIONS

M Brahler, R Georgieva, N Buske, A Muller, S Muller, J Pinkernelle, U Teichgraber, A Voigt, H Baumler. "Magnetite-Loaded Carrier Erythrocytes as Contrast Agents for Magnetic Resonance Imaging." Nano Letters, vol. 6 No. 11, 2006, pp. 2505-2509.*

CG Millan, AZ Castaneda, MLS Marinero, JM Lanao. "Factors associated with the performance of carrier erythrocytes obtained by hypotonic dialysis." Blood Cells, Molecules, and Diseases, vol. 33, 2004, pp. 132-140.*

Allkemper et al., 2002. Contrast-enhanced Blood-Pool MR angiography with optimized iron oxides: effect of size and dose on vascular contrast enhancement in rabbits. *Radiology* 223 (2): 432-438.

Araujo et al., 1999. Influence of the surfactant concentration on the body distribution of nanoparticles. *Journal of colloid and interface science* 6(5): 373-385.

Babincova et al., 2000. Blood-specific whole-body electromagnetic hyperthermia. *Medical Hypotheses* 55(6): 459-460.

Bacri et al., 1990. Ionic ferrofluids:A crossing of chemistry and physics. *Journal of Magnetism and Magnetic Materials* 85:27-32.

Benderbous et al., 1996. Superparamagnetic agents: physicochemical characteristics and preclinical imaging evaluation: Contrast Media Research (CMR). Acad Radiol, 3:S292-S294.

Berry and Curtis, 2003. Functionalisation of magnetic nanoparticles for applications in biomedicine. *J Phys. D: Appl. Phys.* 36: R198-R206.

Bonnemain B., 1998. Superparamagnetic agents in magnetic resonance Imaging: physicochemical characteristics and clinical applications a review. *Journal of Drug Targeting* 6(3): 167-174.

Brahler et al., 2006. Magnetite-loaded carrier erythrocytes as contrast agents for magnetic resonance imaging. *Nano Letters* 6(11): 2505-2509.

Brigger et al., 2002. Nanoparticles in cancer therapy and diagnosis. *Adv. Drug Deliv. Rev.* 54, 631-651.

Davis S.S., 1997. Biomedical applications of nanotechnology-implications for drug targeting and gene therapy. *Trends Biotechnol.* 15: 217-224.

Frank et al., 1993. Enhancement of MR angiography with iron oxide: preliminary studies in whole-blood phantom and in animal. *AJR Am J Roentgenol* 162: 209-213.

Gaur et al., 2000. Biodistribution of fluoresceinated dextran using novel nanoparticles evading reticuloendothelial system. *Int. J Pharm.* 202: 1-10.

Halavaara et al., 2002. Efficacy of sequential use of superparamagnetic iron oxide and gadolinium in liver MR imaging. *Acta radiologica* 43:180-185.

Hilger et al., 2002. Heating potential of iron oxides for therapeutic purposes in interventional radiology. *Acad. Radiol.* 9: 198-202.

Ito et al., 2005. Medical Application of Functionalized Magnetic Nanoparticles. *Journal of Bioscience and Bioengineering*; 100(1): 1-11.

Jain and Vyas, 1994. Magnetically responsive diclofenac sodium-loaded erythrocytes: Preparation and in vitro characterization. *J Microencapsulation* 11(2): 141-151.

Johnson et al., 1998. Gadolinium-bearing red cells as blood pool MRI contrast agents. *Magn. Reson. Med.* 40(1): 133-142.

Jung and Jacobs, 1995. Physical and chemical properties of superparamagnetic iron oxide MR contrast agents: ferumoxides, ferumoxtran, ferumoxsil. *Magnetic Resonance Imaging* 13(5):661-674.

Kreuter J. 1994. Drug targeting with nanoparticles. *Eur. J. Drug. Metab. Pharmacokinet* 19: 253-256.

Kubaska et al., 2001. Dual contrast enhanced magnetic resonance imaging of the liver with superparamagnetic iron oxide followed by gadolinium for lesion detection and characterization. *Clin. Radiol.* 56: 410-415.

Lee et al , Artificially engineered magnetic nanoparticles for ultra-sensitive molecular imaging. Nature Medicine, vol. 13(1): 95-99, Jan. 2007.

Low R.N.; 1997. Contrast agents for MR imaging of the liver. *J Magn. Reson. Imaging* 7(1): 56-67.

Lubbe et al., 2001. Clinical application of magnetic drug targeting.*J Surg. Res.* 95: 200-206.

Magnani et al., 2002. Erythrocyte-mediated delivery of drug, peptides and modified oligonucleotides. *Gene Ther.* 9(11):749-751.

Moghimi et al., 2001. Long-circulating and target specific nanoparticles: theory to practice. *Pharm. Rev.* 53: 283-318.

Morais et al., 2004. Susceptibility investigation of the nanoparticle coating-layer effect on the particle interaction in biocompatible magnetic fluids. *Journal of Magnetism and Magnetic Materials*, 272-276: 2328-2329.

Petri-Fink et al., 2005. Development of functionalized magnetic nanoparticles for interaction with human cancer cells. *Biomaterials* 26: 2685-2694.

Reimer and Tombach, 1998. Hepatic MRJ with SPIO: detection and characterization of focal liver lesions. *Eur. Radiol.* 8: 1198-1204.

Sudimack and Lee, 2000. Targeted drug delivery via the folate receptor. *Adv. Drug Del. Rev.* 41: 147-162.

Vyas and Jain, 1994. Preparation and in vitro characterization of a magnetically responsive ibuprofen-loaded erythrocytes carrier. *J Microencapsulation* 11(1): 19-29.

Wang et al., 2001. Superparamagnetic iron oxide contrast agents: physicochemical characteristics and applications in MR imaging. *Eur. Radiol.* 11 : 2319-2331.

Wilhelm et al., 2003. Intracellular uptake of anionic superparamagnetic nanoparticles as a function of their surface coating. *Biomaterials* 24:1001-1011.

Zhou et al., 2006. Sub-cellular accumulation of magnetic nanoparticles in breast tumors and metastases. *Biomaterials*, 27:2001-2008.

International Search Report for PCT Patent Application No. PCT/EP2007/006349.

Weissleder et al, Superparamagnetic iron oxide pharmacokinetics and toxicity. AJR American Journal of Roentgenology, 152(1):167-173, 1989. XP008088207.

Le et al., "Mathematical modeling provides kinetic details of the human immune response to vaccination", Frontiers in Cellular and Infection Microbiology, (2015), 4(177), pp. 1-13.

Yu et al., "Comparative Immunogenicity of the Tetanus Toxoid and Recombinant Tetanus Vaccines in Mice, Rats, and Cynomolgus Monkeys", Toxins, (2016), 8(194), pp. 1-12.

Zhang et al. "Vaccination with Toxoplasma gondii calcium-dependent protein kinase 6 and rhoptry protein 18 encapsulated in poly(lactide-co-glycolide) microspheres induces long-term protective immunity in mice", BMC Infectious Diseases, (2016), 16:168, pp. 1-11.

* cited by examiner

DELIVERY OF CONTRASTING AGENTS FOR MAGNETIC RESONANCE IMAGING

FIELD OF THE INVENTION

The present invention relates to formulations of MRI contrasting agents, and to the preparation and use of such formulations.

INTRODUCTION

A number of MRI contrasting agents are available for different applications including: the detection of organ damage or pathological modifications, the state and size of lymph nodes, the detection of gastroenteric lesions resulting in bleeding, the presence of tumour masses in brain or other tissues, kidney lesions, and imaging the circulatory system.

Although the more commonly used MRI contrast media are gadolinium (Gd) chelates, these tend to be non-specific, with rapid accumulation in the liver, thereby only allowing short time imaging windows (Kubaska, 2001). The gadolinium chelates show rapid extravasation into the interstitium and are rapidly excreted by the kidneys ($t_{1/2} \approx 1.5$ hours—Allkemper, 2002). Thus, their use needs to be in association with rapid imaging techniques in order to provide the required vessel-to-tissue contrast.

In recent years superparamagnetic nanoparticles have been produced and used as MRI contrasting agents. Superparamagnetic nanoparticles are excellent MRI contrasting agents, superior to gadolinium derivatives, but despite a number of efforts to improve their surface chemistry and biocompatibility, their half life in circulation is short and are rapidly taken up by tissue macrophages that engulf such materials.

The relaxivity of typical SPIO contrast agents is substantially larger than the relaxivity of other paramagnetic molecules such as gadolinium (Jung, 1995). Superparamagnetic iron oxide particles are the first clinically approved liver-specific contrast agents (Low, 1997; Halavaara, 2002) and in the last few years have been used in almost all areas of the biosciences, biotechnology and biomedical applications, including bowel contrast, spleen imaging, lymph node imaging, bone marrow imaging, perfusion imaging and MM angiography (Wang, 2001).

Important properties of magnetic particles for biomedical applications include non-toxicity, biocompatibility, injectability and high-level accumulation in the target tissue or organ, and nanotechnology has now developed to a stage that makes it possible to produce, characterise and specifically tailor the functional properties of magnetic nanoparticles for clinical applications. This has resulted in the improvement of the quality of magnetic resonance imaging and to the manufacture of a variety of iron oxide particles.

Ferrous or ferric oxide is the main constituent of magnetic particles and, given that they are attracted to high magnetic flux density, then they are used for drug targeting and bioseparation processes including cell sorting (Ito, 2005). The particle size varies widely and influences their physicochemical and pharmacokinetic properties (Allkemper, 2002). A distinction is currently drawn between two main superparamagnetic groups of agents (Bonnemain, 1995): SPIOs (superparamagnetic iron oxides), the size of which, including coating, is greater than 50 nm, and USPIOs (ultrasmall superparamagnetic iron oxides) which are smaller than 50 nm. This difference in size is reflected by significant differences not only in the R2/R1 relaxivity ratio but also in plasmatic half-life and biodistribution (Bonnemain, 1998; Reimer, 1998).

Aggregation due to the attractive forces associated with magnetite nanoparticles is prevented by creating an electrostatic double layer, typically by using polymer surfactants functioning as a steric stabiliser, such as dimercaptosuccinic acid (DMSA) (Morais, 2004), polysaccharide polymer (dextran or dextran derivatives), starch, polyvinyl alcohol (PVA), polyethylene oxide (PEO), polyethylene glycol (PEG) or by modifying the isoelectric point with a citrate or silica coating (Cornell, 1991; Bacri, 1990). The most commonly used iron oxide nanoparticles are dextran coated, and are physiologically well tolerated (Babincova, 2000).

Magnetic nanoparticles are also potential target-specific agents for given pathologies, since a drug immobilised on magnetic materials could be transported through the vascular system and be concentrated at a particular point in the body under the action of an external magnetic field. To enhance target specificity, the drug is generally associated with another molecule capable of specific recognition and binding to the target site. The most common type of associated molecules are antibodies (and their fragments), lectins, proteins, hormones, charged molecules and some low molecular weight ligands such as folate (Sudimack, 2000; Petri-Fink, 2005). A highly publicised example of magnetic drug delivery is as a replacement or to augment chemotherapy/radiotherapy treatment (Lubbe, 2001; Hilger, 2002; Zhou, 2006).

SPIOs may be injected intravenously, relying on blood circulation to transport the particles to the region of interest. Alternatively, in many cases, the particle suspension (ferrofluid) is injected directly into the general area where treatment is desired. Either of these routes has the requirement that the particles do not aggregate and block their own spread.

Diffusion to the general tissue mass is presumably aided by pressure gradients from the blood vessels to the tissue spaces. Larger particles of 50-100 nm diameter did not transport in this way and remained in circulation or attached to the walls of the vascular system, with the concomitant risk of thromboses (Berry, 2003).

Moreover, following SPIO intravenous administration, SPIOs are rapidly coated by serum proteins (Davis, 1997). This opsonisation process renders the particles recognisable by the body's major defence system, the reticuloendothelial system (RES). The RES is a diffuse system of specialised phagocytic cells that are associated with the connective tissue framework of the liver, spleen and lymph nodes (Kreuter, 1994; Araujo, 1999). The macrophages (Kupffer) cells of the liver and spleen play a critical role in the removal of opsonised particles. Thus, the application of nanoparticles in vivo would require surface modification that would ensure particles were stable to the RES. The literature reports both coating nanoparticles with different molecules and strategies that attempt to inhibit the opsonisation of plasma components, thereby permitting longer circulation times (Brigger, 2002; Moghimi, 2001).

Since the uptake rate of SPIO into the reticuloendothelial system is inversely related to its particle size (Alikemper, 2002) minimising the particle surface results in a decreased protein absorption, which reduces particle phagocytosis, finally resulting in a prolonged intravascular retention.

Whatever the ferrofluid's parameters, the infusion route, such as the duration and rate of the injection, and physiological parameters, need to be considered for these new forms of pharmacological application. Moreover, there are fundamental problems associated with the use of magnetically directed drug targeting. Targeting, for example, to a specific cell type, may be possible with directed coatings, but retaining the particles in the vicinity of the cell membrane for any length of time is difficult, as the cell tends to automatically initiate receptor-mediated endocytosis (Wilhelm, 2003).

Although a wide range of size and materials has been explored to prolong the circulation time or to enhance target specificity of nanoparticles, their applications are limited by an RES that is highly efficient in removing circulating foreign objects, and successful avoidance of this has not yet been possible (Gaur, 2000).

Studies have also been made on ferrofluids encapsulated in erythrocytes to obtain the targeting of the entrapped drug to the site of action. Sprandel et al., have described the magnetisation of erythrocyte ghosts, while Vyas et al. have loaded erythrocytes with ibuprofen and magnetite using the pre-swell technique. These studies were performed in vitro, and have reported that it is possible to entrap drug and magnetite in erythrocytes. However, they showed a very high efflux of almost the entire entrapped magnetite, due to its cytotoxic and haemolytic effect on the cells (Vyas, 1994).

Erythrocytes have been proposed as a novel drug carrier and are recognised as potential biocompatible vectors for different bioactive substances such as drugs, enzymes and peptides (Magnani, 2002). The encapsulation of drugs or biologically active agents can be performed for example by the method described in U.S. Pat. No. 6,139,836 (US patent; Magnani et al.). Some studies have also reported the preparation of magnetically responsive erythrocytes for drug targeting by co-encapsulation of a drug with certain ferrofluids such as magnetite (Vyas, 1994). Further applications of the carrier erythrocytes are their possible use as contrast agents for MRI, for example gadolinium DTPA dimeglumine (Gd-DTPA) has been encapsulated in human and rat erythrocytes (Johnson, 1998).

Contrast agents incorporating superparamagnetic iron-oxide (SPIO) nanoparticles have shown promise as a means to visualise labelled cells using MRI. Recently, SPIO nanoparticles have been provided for the diagnosis and monitoring of various cardiovascular diseases including, but not limited to, atherosclerosis, thrombosis, ischaemia, and for cellular cancer therapy. The commercially available standard SPIOs, such as SHU 555A (Resovist, from Schering), are extremely strong enhancers of proton relaxation, but have very short useful half-lives after intravenous administration, as they are rapidly cleared from the blood within minutes and accumulate in the reticuloendothelial cells of the liver and spleen.

U.S. 2005/0261575 discloses positive contrast MRI of magnetically tagged cells, objects and tissues.

WO 2006/012201 discloses nanoparticles for imaging atherosclerotic plaques.

U.S. 2004/0076586 discloses compositions and methods for delivering pharmaceutically active agents using nanoparticulates.

U.S. Pat. No. 6,933,331 discloses nanotechnology for drug delivery, contrast agents and biomedical implants.

U.S. Pat. No. 4,669,481 discloses methods of magnetic resonance imaging using chromium-labelled red blood cells.

WO 2006/048321 A1 discloses diagnostically active substances including nanoparticles that can be introduced into biological cells.

WO 91/16080 A1 discloses chelates of Gadolinium or Iodum that could be encapsulated into erythrocytes as contrast agents.

U.S. Pat. No. 5,928,958 describes iron-based superparamagnetic particles with sizes ranging from 3-50 nm and from 10-100 nm.

U.S. 2006/0078502A describes an MRI contrast agent comprising a complex of a paramagnetic cation, such as $Gd^{3+}$, $Dy^{3+}$ and $Fe^{3+}$.

Intense efforts are ongoing in the development of biocompatible magnetic carriers for the directed transport and controlled release of drugs.

SUMMARY OF THE INVENTION

Surprisingly, we have now found that superparamagnetic iron oxide particles can be encapsulated in erythrocytes through the use of a permeabilising amount of a hypotonic dialysis solution.

Thus, in a first aspect, the present invention provides a viable erythrocyte containing cytosolic superparamagnetic iron oxide in nanopartiuclate form.

It is preferred that the amount of superparamagnetic iron oxide (SPIO) is present in the erythrocytes in an amount sufficient to allow magnetic resonance imaging (MRI) when a preparation of a plurality of such erythrocytes is injected into an individual. When concentrations of SPIO in the erythrocytes is relatively low, or smaller amounts of erythrocytes are used, then MRI may only be possible after an external magnetic source has been employed to attract the SPIO-containing erythrocytes to a particular location. For guidance, although the skilled practitioner will readily be able to discern appropriate levels, the amount of SPIO, in terms of the amount of iron, in the erythrocytes should be between about 1 mM and 40 mM, with the preferred range being between about 3 mM and 20 mM.

It will be appreciated that the present invention provides a preparation of erythrocytes containing cytosolic SPIO. Such a preparation may be appropriate for immediate use for injection into a patient for MRI purposes, or may be subsequently made up for such use, and may be in a freeze-dried state, for example. If freeze-dried, then it is desirable to incorporate one or more substances in the preparation to inhibit or prevent membrane degradation, such as propylene glycol.

By 'cytosolic' is meant that the SPIO particles are present in the cytosol rather than, for example, endocytic vesicles, such as would be obtained by the process of endocytosis or phagocytosis.

It is further preferred that the erythrocytes of the present invention comprise one or more drugs, such that the erythrocytes may be used as drug delivery vehicles. Such drugs may be used as described above, and may be associated with the SPIO particles, or carried on or in the erythrocytes. Particularly preferably, the drugs are such as to be effective when erythrocytes are targeted to a specific area by the use of external magnetism, and it is further preferred that the drugs may be released by the application of external magnetism, such as by rupturing the erythrocytes through the effects on the SPIO particles.

It is preferred that the SPIO particles may be co-entrapped into erythrocytes with at least one of several categories of pharmaceutically active agents, ingredients or drugs, including, but not limited to: anti-inflammatory and immunosuppressive drugs, such as glucocorticoid analogues; antiviral or antiretroviral drugs such as Nucleoside/Nucleotide Reverse Transcriptase Inhibitors (NRTIs), Non-Nucleoside Reverse Transcriptase Inhibitors (NNRTIs), Protease Inhibitors, and/or fusion or entry Inhibitors; anticancer drugs such as chemotherapeutic agents, for instance antracyclins, intercalating agents, Thyrosine kinase inhibitors, Methyltransferase inhibitors, deacetylase inhibitors, and proteasome inhibitors; oligonucleotides; monoclonal antibodies, peptides and peptide nucleic acids; photosensitizing drugs; and infra red fluorescent agents. It is also preferred that combinations or mixtures of any of the above can also be used. Specific examples of said drugs will be known to the skilled person.

Nanoparticles and drugs and/or other nanomaterials can be co-encapsulated within erythrocytes for drug targeting and/or drug release and/or cell destruction if the encapsulated material causes local heating upon external radiation, for example.

In this way, drugs that may otherwise be non-specific and toxic to other tissues can be carefully targeted. Thus, toxins, chemotherapeutic agents and antibodies are preferred drugs for use in the present invention.

BRIEF DESCRIPTION OF THE INVENTION

Figure 1:
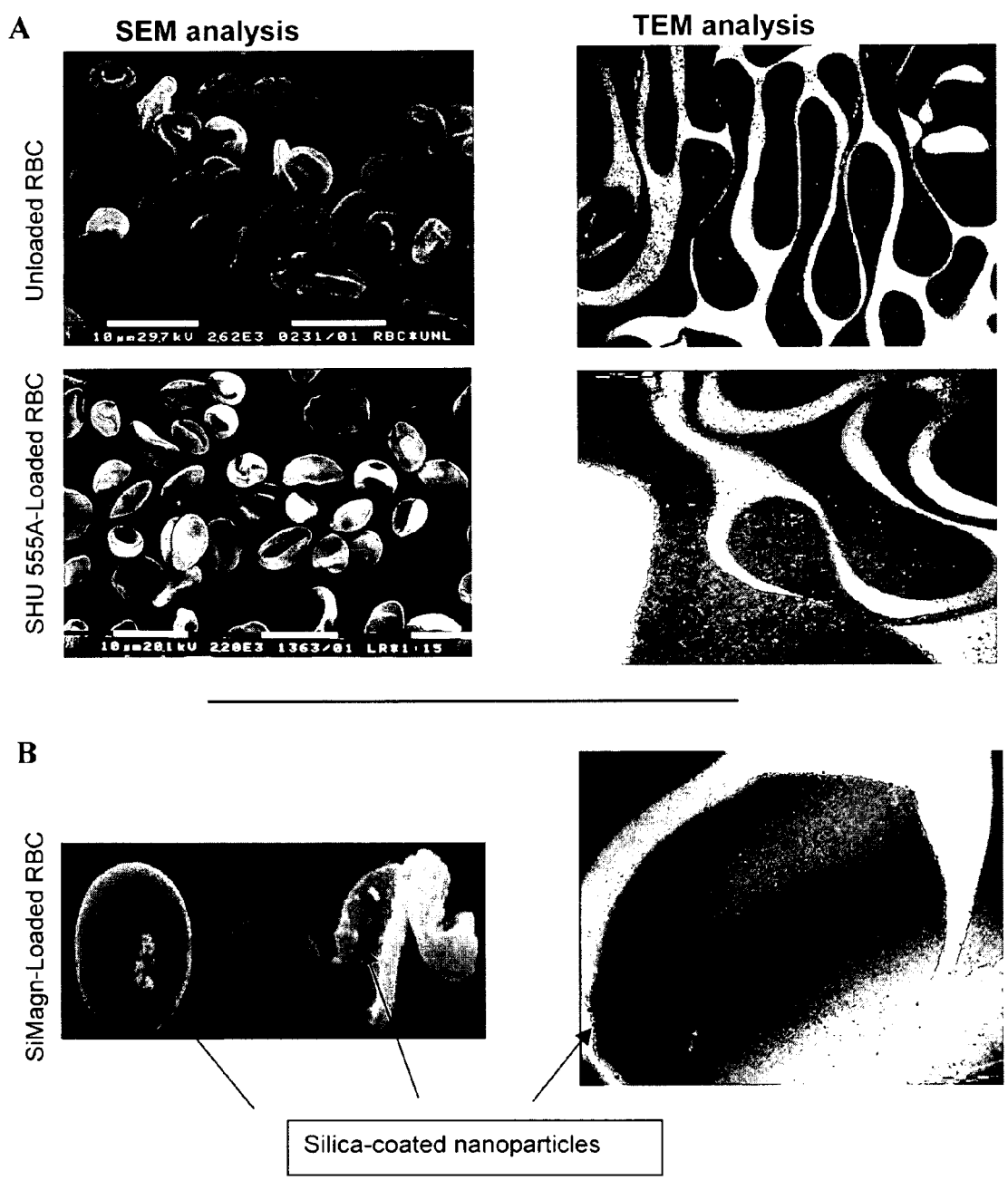
FIG. 1A are electronic transmission microscopic analysis perspective view images illustrating SEM analysis and TEM analysis of unloaded RBC and SHU 555A-Loaded RBC dispersed in cytoplasm.
FIG. 1B are electronic transmission microscopic analysis perspective view images illustrating SiMagn-Loaded RBC with silica-coated nanoparticles dispersed in cytoplasm.

By the term 'viable' is meant an erythrocyte that is still recognised as viable by the host into which it is injected. Non-viable, or dead, erythrocytes, such as the crenated erythrocytes prepared in the art, are immediately recognised as non-viable and are eliminated from the host system. The advantage of the erythrocytes of the present invention is that they are able to survive for a number of days without being eliminated, and often have a lifespan comparable to that of untreated erythrocytes. In this regard, the RBCs (red blood cells) may also be referred to as stable erythrocytes. In particular, it is preferred that the RBCs can substantially avoid immune clearance and that around at least 50%, and more preferably at least 60% to least 70% or 80% of the loaded RBC's have statistically significant comparable lifespans in vivo to unmodified RBC's.

The terms red blood cells and erythrocytes are used interchangeably herein.

The cytosolic superparamagnetic iron oxide is also referred to herein as encapsulated or substantially internalised superparamagnetic iron oxide, or encapsulated or substantially internalised SPIO, and is distinct from vesicular or micellar SPIO. The size of the particles is discussed herein below, but is not restricted to SPIO, and the range of sizes includes USPIO. It is preferred that the total size of each particle, including any coating, such as dextran, is no greater than 80-90 nm, and is preferably between 20 and 60 nm, more preferably between 3 and 50 nm, more preferably between 10 and 100 nm, more preferably between 10 and 30 nm, more preferably between 20 and 50 nm, more preferably between 50 and 80 nm, and most preferably between 40 and 60 nm.

It will be understood that the present nanoparticles can also be referred to as SPION (SPIO Nanoparticles).

As further discussed in the Results section of the Examples, previous attempts in the prior art have resulted in erythrocytes that show contrast material on the cell surface. This membrane modification could leads to immune clearance due to opsonisation of the erythrocytes. The present invention, however, avoids this by substantially internalising the contrast agent nanoparticles within the cytoplasm of the cell. WO 2006/048321 A1 relates to the incorporation in mammalian cells (including blood cells and thus erythrocytes) of active substances and diagnostically active substances in the form of nanoparticles. However, a recent paper from the same applicants and others (Nano Letters 6, 2505-2509, 2006) demonstrate that the method proposed generates erythrocytes that contain nanoparticles bound to the membrane. Therefore, the cells are surface modified and the presence of adsorbed contrast agent nanoparticles on the cell surface leads to immune clearance. Thus, this method does not result in viable or stable erythrocytes.

WO 91/16080 A1 (Guerbet) is an old publication and relates to a contrast agent encapsulated into erythrocytes by a lysis resealing technique. The focus of the application is towards the use of chelates of Gadolinium or Iodum as the contrast agent. There is brief reference to contrast agents including superparamagnetic colloids, but no further discussion thereof or experimental work on this, as evidenced by the fact that issues such as dispersion are ignored. Furthermore, no mention of nanoparticles is made and, indeed, no reference to the possible size of these superparamagnetic colloids is reported.

Since this publication, it has become apparent that superparamagnetic colloids can actually result in erythrocyte interactions and damage. Thus, this publication does not teach viable erythrocytes, nor does it describe the use of nanoparticles. Furthermore, their method of encapsulation is a lysis resealing technique. Based on their work with Gadolinium and Iodide, the authors merely speculate that a similar behaviour could have been followed by other contrasting agents including iron oxide. However, recent evidence (including the paper in Nano Letters supra) teaches against this and it is now clear that conditions based on those appropriate for Gadolinium chelates and Iodine-containing molecules are not suitable for SPIO nanoparticles.

In contrast, the present inventors have surprisingly found that SPIO can provide at least one of the following separate but complimentary advantages. Firstly, the erythrocytes of the present invention are not cleared by the immune system when loaded with the paramagnetic material, which is a significant advantage over erythrocytes which have even a small amount of paramagnetic material bound to their cell surface. This provides the present erythrocytes with an improved life span in vivo therefore significantly aiding MRI diagnosis in a clinical setting where delays can occur and also allows the erythrocytes to enter deep into body tissues. Indeed, the increased stability and viability of the erythrocytes allows the same patient to be imaged on number of occasions over time, thereby allowing a time-lapsed data set to be obtained, which could be used to study drug efficacy over several days or even weeks.

A further and quite unexpected advantage is that we have discovered that superparamagnetic nanoparticles encapsulated, or loaded, into RBCs generate (under identical conditions) a T2* relaxation time significantly lower than the signal measured by adding the same amount of nanoparticles to an identical RBC (Red Blood Cell) suspension or to intact blood. By lowering the T2* relaxation time, the resolution of the MRI image is improved. This will aid physicians detect even smaller tumours, for instance.

It is particularly preferred that the superparamagnetic nanoparticles have the general formula $Fe_2^{3+}O_3M^{2+}O$ where $M^{2+}$ is a divalent metal cation such as ferrous iron, manganese, nickel, cobalt or magnesium.

Preferably, the SPIO is magnetite. This occurs when the metal ion ($M^{2+}$) is ferrous iron ($Fe^{2+}$), giving superparamagnetic nanoparticles of the formula $FeFe_2O_4$. Thus, it is preferred that $M^{2+}$ is ferrous iron ($Fe^{2+}$).

However, it is also preferred that the SPIO comprises alternatives to ferrous iron, although it will be understood that this is for $M^{2+}$ and that the SPIO is still an oxide of iron. In other words, only the $M^{2+}$ is substituted, not the $Fe_2^{3+}$ element of the SPIO general formula $Fe_2^{3+}O_3M^{2+}O$. Thus, other non-magnetite based SPIOs are also preferred.

Thus, it is particularly preferred that $M^{2+}$ is at least one of the following divalent cations, selected from the group consisting of manganese, nickel, cobalt, and magnesium. This provides $MnFe_2O_4$, $NiFe_2O_4$, $CoFe_2O_4$ and $MgFe_2O_4$, as taught in Nature Medicine, Vol. 13, number 1, page 95-99, January 2007(Jae-Hyun Lee et al.) and in Eur. Radiol. Vol. 11, page 2319-2331, 2001 (Yi-Xiang J. Wang et al.). Manganese, giving $MnFe_2O_4$, is particularly preferred as it provides a strong Magnetic Resonance contrast effect, due to its high relaxivity value.

The present invention further provides a process for the preparation of one or more erythrocytes as defined herein, the said process comprising dialysis of a preparation of the said erythrocytes against a hypotonic buffer sufficient to permeabilise the erythrocytes, and wherein said preparation comprises monodispersed SPIO, and subsequently resealing the erythrocytes.

The loading of magnetic nanoparticles into erythrocytes using the procedure of the invention occurs through pores in the RBC membrane arising from dialysis of the RBC suspension in an hypotonic buffer. This is different from that described in previous reports were the authors have reported the entrapment of ferrofluids in erythrocytes by a technique that produced crenated ghost cells (Jain, 1994) with limited stability.

The term 'monodispersed' indicates that the particles of SPIO are treated such as not to agglomerate, and it is preferred to obtain the SPIO pre-prepared in such a fashion, rather that to treat the SPIO within the preparation of erythrocytes. It is particularly preferred that the SPIO nanoparticles are sufficiently small that they can readily pass into the erythrocytes when they become porous on exposure to the hypotonic buffer. Such nanoparticles are preferably coated in dextran, although any other means for obtaining monodispersion are also envisaged by the present invention. Monodispersed magnetic nanomaterial PMP-50, sold by G. Kisker GbR, is preferred. A particularly preferred ferrofluid is that sold by Schering as SHU 555A (Resovist).

The hypotonic buffer may be present in any concentration suitable to achieve poration of the erythrocytes. If the osmolarity of the hypotonic buffer is too high, then poration may not happen, whilst if the osmolarity is too low, then excessive damage can occur to the erythrocytes, and insufficient viable cells recovered. Thus, by way of a guide, an osmolarity of between 60 and 120 mOsm is preferred, with a range of 70 to 110 mOsm being more preferred.

It has been found that recovery rates of in excess of 70% of erythrocytes exposed to a hypotonic buffer can be achieved whilst obtaining sufficiently high internal concentrations of SPIO where the osmolality of the erythrocytes does not fall below 90 mOsm after treatment.

The volume of the buffer as a ratio to the preparation of erythrocytes is preferably between about 15 and infinity, with a range of between about 20 and 100 being more preferred and a range of 40-80 being particularly preferred.

The nature of the buffer is not particularly important, provided that it is not harmful to the erythrocytes for the patient in such a way as to either drastically reduce the number of erythrocytes surviving the treatment or to be toxic to the patient in an undesired manner. Suitable buffers include carbonate and phosphate buffers.

In order to obtain a satisfactory degree of viability for the erythrocytes, it is preferred to use a hypotonic buffer comprising ingredients to ensure the continued well-being of the erythrocytes whilst porated. In this respect, the presence of a balanced pH, preferably at about 7.4, is preferred, together with glucose and ATP. Other ingredients may also be incorporated, such as glutathione, in order to enhance the viability and recovery of viable erythrocytes.

The duration of exposure of the erythrocytes to the hypotonic buffer may be as long as desired, but is preferably between 20 minutes and 5 hours, more preferably between 30 minutes and 4 hours, and more preferably 1 hour to 3 hours. It is particularly preferable to minimise the amount of exposure as far as possible, whilst ensuring the uptake of the maximum amount of SPIO, as porated erythrocytes are vulnerable.

Resealing of the treated erythrocytes is performed by known techniques after removing the dialysis buffer. It is preferred that, after the resealing, the erythrocytes are washed to remove any extracellular SPIO. A suitable washing agent is Hepes buffer. The erythrocytes may then be stored in Hepes buffer or any other suitable solution, such as artificial plasma, prior to use.

The present invention further provides the use of a preparation of erythrocytes as defined herein in a magnetic residence imaging technique.

The present invention further provides the use of a preparation of erythrocytes as defined herein in the treatment of a condition wherein erythrocytes of the invention are localisable in the vicinity of an area to be treated by external magnetic force.

It will be appreciated that erythrocytes may be from any animal, but are preferably from a mammal, and particularly preferably from a human. Likewise, the subject to be treated or imaged may be animal, preferably mammal, and particularly preferably human. Although it is preferable to use erythrocytes from the patient, it is also acceptable to use erythrocytes prepared from a compatible donor and, particularly preferably, a universal donor.

The present invention further provides a method of removing red blood cells from a patient and optionally separating them from other blood cells and optionally the serum, loading the red blood cells with SPIO and reintroducing the red blood cells into the patient. Preferably, the red blood cells can be stored at any stage, and most preferably, once they have been loaded with SPIO, so as to allow a pre-prepared store of loaded erythrocytes useful in emergency situations, for instance. In such cases, it is preferred that the erythrocytes are universal donor, blood type O.

Methods of resonance imaging are also provided, comprising administering the present RBCs loaded with SPIO. The method also preferably comprises removing red blood cells from a patient and optionally separating them from other blood cells and optionally the serum, loading the red blood cells with SPIO and reintroducing the red blood cells into the patient. Preferably, the red blood cells can be stored at any stage, and most preferably, once they have been loaded with SPIO, as above.

Also provided is a method to lower the T2* relaxation time of superparamagnetic iron oxide by encapsulation thereof in erythrocytes, said encapsulated erythrocytes being viable.

In a further aspect, there is provided a method of increasing the resolution of resonance imaging of superparamagnetic iron oxide, by encapsulation of superparamagnetic iron oxide in viable erythrocytes.

In a still further aspect, there is provided a pharmacologically active preparation comprising superparamagnetic material encapsulated in viable erythrocytes, suitable for administration to patient for resonance imaging.

Thus, we have now found a strategy for loading SPIO nanoparticles in human erythrocytes in a manner that avoids RES clearance, and which offers a novel approach for intravascular drug delivery and blood pool imaging. We have found, unexpectedly, that superparamagnetic nanoparticles can be encapsulated within human erythrocytes in amounts high enough to be useful as contrasting agents and that these constructs are stable. In contrast to superparamagnetic nanoparticles, these particle-loaded erythrocytes are not recognised by macrophages unless they are at the end of their physiological life or unless specifically modified.

These superparamagnetic iron oxide loaded erythrocytes are artificial constructs useful as contrasting agents, especially for imaging of the circulatory system and in the detection of occluded vessels or altered angiogenesis in defined body areas or damaged vessels resulting in bleeding.

The present invention provides human erythrocytes loaded with superparamagnetic nanoparticles useful as MRI contrasting agents, especially in the imaging of the circulatory system. Said erythrocytes can also contain one or more drugs co-encapsulated with said superparamagnetic nanoparticles and can be driven by an external magnetic field to release the encapsulated drug within selected organs or preferentially in selected body districts.

The present invention will now be described with reference to the following, non-limiting Examples. All references cited herein are incorporated by reference unless otherwise apparent and to the extent that they complement the teaching of the present application.

EXAMPLES

Materials and Methods

Materials

Erythrocytes loading procedure was performed with a commercially available ferrofluid SHU 555A (Resovist, 0.5 mmol Fe/ml) obtained from Schering pharmaceutical company, consisting of superparamagnetic iron oxide nanoparticles carboxydextran coated, 60 nm in diameter.

This particulate suspension is generally used to enhance the signal from magnetic resonance imaging (MRI) examinations. Silica coated magnetite nanoparticles suspension, SiMagn (27 mg/ml) with a size of around 40-140 nm was also used.

Encapsulation of Magnetic Nanoparticles in Human Erythrocytes

Human blood was collected from healthy volunteers into heparinised tubes.

Red blood cells (RBCS) were isolated by centrifugation at 1400 g at 4° C. for 10 min from freshly drawn blood. The serum and buffy coat were removed and the packed cells were washed three times with Hepes buffer (10 mM Hepes, 140 mM NaCl, 5 mM glucose, pH 7.4) and then resuspended in the same buffer at a 70% haematocrit. These cells were dialysed in presence of magnetic nanoparticles for 75 min using a tube with a 12-14 kDa cut-off in 50 vol of 10 mM $NaHCO_3$, 10 mM $NaH_2PO_4$, 20 mM glucose, 4 mM $MgCl_2$ pH 7.4, containing 2 mM ATP and 3 mM reduced glutathione. The osmolarity of dialysis buffer was 64 mOsm.

All these procedures were performed at 4° C. under sterile conditions. Resealing of RBC was obtained by adding 0.1 vol of 5 mM adenine, 100 mM inosine, 2 mM ATP, 100 mM glucose, 100 mM sodium pyruvate, 4 mM $MgCl_2$, 194 mM NaCl, 1.606 M KCl, 35 mM $NaH_2PO_4$, pH 7.4 (PIGPA) per vol of dialysed RBC and by incubating at 37° C. for 45 min.

The resealed cells were recovered by centrifugation at 400 g and washed four times with Hepes buffer to remove unentrapped magnetic particles.

Following the same procedure unloaded erythrocytes (UL-RBC) were prepared, with the exception that they were dialysed in absence of magnetic material.

Then the magnetic susceptibility of the loaded erythrocytes (L-RBC) and other different parameters were evaluated.

Magnetite Concentration

Erythrocytes were loaded using different amounts of SHU 555A (0.5 mmol Fe/ml or 28 mg/ml).

1 ml of RBC has dialysed both in presence of 5.6 mg Fe (200 μl) (L1-RBC) and 22.4 mg Fe (800 μl) (L2-RBC). The loading efficiency was evaluated by different parameters.

In Vitro Characterisation of SHU 555A-Loaded Erythrocytes;

Percentage Cell Recovery

Percentage cell recovery was determined by counting the number of total intact erythrocytes before and after magnetite loading using a hemocytometer.

Assessment of Cell Integrity

To determine whether the loaded cells retained the properties of native red cells, several features of cell integrity were examined. Mean corpuscular volume, mean haemoglobin concentration, and mean corpuscular haemoglobin concentration were measured with an automated cytometer (Model MICROS O.T, HoribaABX Diagnostics, Italy).

Magnetic Responsiveness $1 \times 10^9$ loaded erythrocytes were placed in a micro tube and their magnetic responsiveness was evaluated by an incubation near to a magnet of 3000 Gauss. The magnetic erythrocytes localised at the site of magnet application were separated from RBC non attracted by washing in Hepes buffer, collected and counted by an automated cytometer and the percentage of attracted cells were calculated respect to initial number cells.

NMR Relaxation Measurements of Loaded Erythrocyte Suspensions and Determination of the Entrapped Magnetite Concentration.

The magnetite concentration in loaded erythrocytes was determined by NMR relaxation measurements using a dose-response curve generated by adding known amounts of SHU 555A contrast agent to human and murine blood samples. The concentration range studied was 0 to 15 mM Fe with at least 9 concentration levels. The longitudinal ($T_1$) and transverse ($T_2$) relaxation times of these samples at 44% of haematocrit were measured at magnetic field strength of 4.7 Tesla at 37° C. using an AC-200 NMR-Bruker spectrometer. $T_1$ was measured using a 180°-τ-90° inversion recovery sequence with a fixed relaxation delay of at least $5 \times T_1$. The times of inversion (τ) were chosen on the basis of an estimated $T_1$ value. $T_2$ was measured using the Carr-Purcell-Meiboom-Gill method (CPMG). The echo-times were chosen on the basis of an estimated $T_2$ value.

The values of $(1/T_1^c - 1/T_1^0)$ (where $T_1^c$ is the relaxation time at the concentration [c] of contrast agent and $T_1^0$ the relaxation time of the RBC sample without SHU 555A) were plotted versus the concentration of SHU 555A and were fitted by least squares method to a straight line, the slope of which is the longitudinal relaxivity (r1).

Two different r1 values were obtained in two concentration ranges: $r1=2.49$ $sec^{-1}$ $mM^{-1}$ in the range 0.1 mM<[c]<1 mM and $r1=1.95$ $sec^{-1} mM^{-1}$ in the range 1 mM<[c]<15 mM.

The transversal relaxivity (r2) was calculated in a similar way in the interval 0.1 mM<[c]<0.3 mM by plotting the values of $(1/T_2^C - 1/T_2^0)$ versus [c] resulting in $r2=153.6$ $sec^{-1}$ $mM^{-1}$. All analysis was performed in EXCEL (Microsoft Corporation).

For the correlation to be considered linear the following criteria were defined: correlation coefficient (R squared) greater than 0.990 and the distribution of points around the regression curve must be randomly distributed.

Consequently, it was possible to estimate the concentration of SHU 555A encapsulated in the erythrocytes by using the inverse formula $[c]=(1/T_1 - 1/T_1^0)/r1$ and $[c](1/T_2 - 1/T_2^0)/r2$ in correspondence of the measured $T_1$ and $T_2$ values of loaded erythrocyte suspensions at haematocrit of 44%.

We also determined the $T_2^*$ value, obtained from the NMR FIDs measured at 37° C., in suspension samples of control RBCs, L1-RBC and in a sample of control RBC mixed to the same quantity of SHU 555A agent L1-RBC incorporated.

Morphology

Normal, unloaded and loaded erythrocytes were examined by Transmission Electron Microscopy (TEM) and Scanning Electron Microscopy (SEM). For TEM analysis cells were quickly washed in 0.1 M Sörensen phosphate buffer pH 7.3, sedimented at 600 g and immediately fixed in 2.5% glutaraldehyde in the same buffer for 1 h. The cells were then postfixed in 1% OsO4 in phosphate buffer, dehydrated with ethanol and embedded in araldite. Thin sections were collected on nickel grids, stained with uranyl acetate and lead citrate, and analysed with a Philips CM10 electron microscope. For SEM analysis, RBCs were washed and fixed in suspension with 2.5% glutaraldehyde in Sörensen buffer and drops of the suspension were deposited on poly-Lysine-coated cover slips. The adhesion was carried out overnight in a moist and sealed chamber at 4° C. The slides were then washed and postfixed 1% OsO4 in phosphate buffer for 1 h.

A gentle progressive alcohol dehydration was performed and specimens were critical point-dried.

After mounting on conventional SEM stubs by means of silver glue, slides were gold-coated by a sputtering device. Observations were carried out with a Philips 515 scanning electron microscope.

In Vitro Stability

Loaded cells were resuspended at a haematocrit of 6% in phosphate-buffered saline, PBS (154 mM NaCl, 5 mM $K_2HPO_4/NaH_2PO_4$, pH 7.4) containing 5 mM glucose, plated in petri dishes and incubated at 37° C. At various time intervals the samples were removed and packed by centrifugation at 600 g for 10 min.

Haemoglobin released in the sample supernatants was measured at 540 nm spectrophotometrically, and percentage haemolysis was determined by comparing the absorbance of supernatant with the absorbance obtained after complete haemolysis of same number of cells in distilled water.

Moreover, the pellets of these samples diluted in Hepes buffer at a haematocrit of 44% were characterised by relaxivity NMR measurements.

Recognition of Magnetic Nanoparticles-Loaded RBCs by Human Macrophages

Human monocyte-derived macrophages from blood samples of healthy donors were obtained by separation in Lymphoprep solution (specific density 1.077; Axis-Shield PoC AS, Norway).

Monocytes were separated from lymphocytes by adherence to plastic dishes overnight at 37° C. After removal of nonadhering cells by repeated washes, cells were cultured in RPMI 1640 medium supplemented with 10% (v/v) heat-inactivated fetal calf serum (FCS), 1% antibiotics (penicillin/streptomycin), and 2 mM L-glutamine at 37° C. in a humidified 5% $CO_2$ atmosphere. The culture medium was changed every 2 days and after 7 days of culture the great majority of the adherent cells were differentiated macrophages. Magnetic nanoparticles loaded-RBCs were prepared by a dialysis of RBC in presence of 6 mg of SHU 555A or SiMagn nanoparticle suspensions.

$1 \times 10^6$ macrophages were incubated for 16 h in the presence of SHU 555A-loaded RBC or SiMagn-loaded RBC or unloaded RBC at a ratio of 100 RBC per macrophage. After this time, RBC were carefully removed by repeated washes and macrophages were fixed in methanol and observed after May-Grunwald Giemsa stain by an Olympus IX51 light microscope.

In Vivo Studies

Animal Preparation

Female Balb/C mice (Nossan, Milan, Italy) were housed at 22±1° C. with a 12-h light/dark cycle, 60±5% humidity, and 12 air changes/h.

In the pharmacokinetic experiments each mouse received intraperitoneally 250 µl of a suspension of loaded-RBC at 10% of haematocrit, derived from an erythrocyte suspension containing 1.5 µmol of paramagnetic iron/ml RBC.

After the end of injection, the withdrawals of blood samples from ocular arteries have been done at 2, 3, 6, 10, 13 days and aliquots of whole blood were analysed by NMR measurements.

Results

The results shown in FIG. 1 indicate that it is possible to encapsulate monodispersed magnetic nanomaterials in human erythrocytes, especially those having an average size of 40-60 nm, and that the resulting cells, after the procedure, have normal morphology. In fact, no significant differences in cell morphology, as observed by scanning electron microscopy (SEM), were observed, with respect to control cells. The majority of erythrocytes appeared to have a biconcave discoid shape, with occasional stomatocytes and rarer echinocytes.

Using electronic transmission microscopic analysis, the presence of nanoparticles was evaluated in at least 10 frames. For each field a central area of specimens was selected in which erythrocytes appeared homogeneously distributed. Microscopic analysis showed a similar morphologic aspect in all RBC loaded samples; each field presented a least 60% of erythrocytes containing magnetic nanoparticles, dispersed in cytoplasm (FIG. 1A).

The loaded erythrocytes were slightly smaller on average than the untreated cells (MCV 78.5 and 60 versus 87 fl, respectively for L1-RBC and L2-RBC), with less haemoglobin per cell (MCH 20.1 and 16 versus 28 pg), but with a near normal mean cellular haemoglobin concentration (MCHC 31 and 28 versus 33 g/dl). It should be noted that the reduced MCV reported above is due to the dilution of RBC applied in these loading procedures (i.e. for L2 RBC: 1 ml RBC at 70% haematocrit with 800 µl of SHU 555A) and not to the use of SHU 555A, as similar values were observed when unloaded erythrocytes were prepared using identical dilutions.

The total preparation procedure typically resulted in a cell recovery of loaded erythrocytes ranging from 60% to 70%, similar to that for unloaded cells. This percentage of cell recovery is higher than the value obtained by other authors (Vyas, 1994; Johnson, 1998). The loaded erythrocytes were responsive to the external magnetic field, and maintain their magnetic susceptibility for several days.

The results obtained are unexpected since the prior art teaches that all previous attempts to encapsulate nanomaterials within erythrocytes result in at least some nanoparticles bound on the external erythrocyte membrane. However, the presence of surface-bound nanoparticles leads to immediate immune clearance via the RES.

For instance, WO 2006/048321 discloses diagnostically active substances including nanoparticles that can be introduced into biological cells but these nanoparticles are partially adsorbed onto the external surface of the erythrocyte membrane. This is clearly documented by the same inventors in Nano Letters 6, 2006 pag. 2505-2509. This occurs if the nanomaterials are made of silica-coated Superparamagnetic nanoparticles (FIG. 1B) or nanoparticles are not monodispersed.

netite-loaded RBC containing nanoparticles bound onto the external erythrocyte membrane are actively recognized and phagocytosed by macrophages. (FIG. 2)

Figure 2:
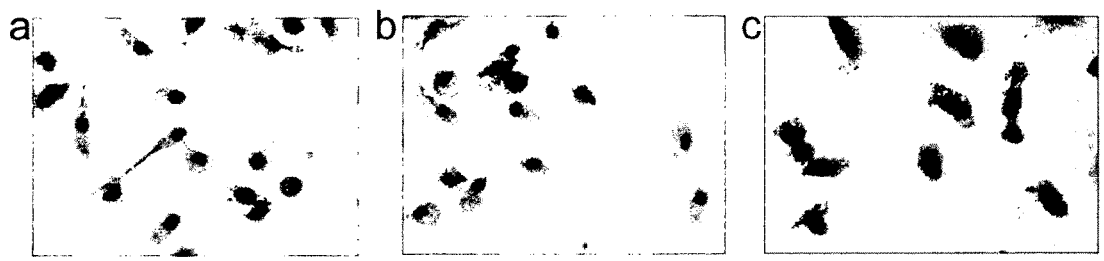
FIG. 2a is an electronic transmission microscopic analysis perspective view image illustrating human macrophages that were incubated for 16 hours at 37° C. with unloaded erythrocytes.
FIG. 2b is an electronic transmission microscopic analysis perspective view image illustrating human macrophages that were incubated for 16 hours at 37° C. with SHU 555A-Loaded erythrocytes.
FIG. 2c is an electronic transmission microscopic analysis perspective view image illustrating human macrophages that were incubated for 16 hours at 37° C. with SiMagn-Loaded erythrocytes.

FIG. 2 shows human macrophages that were incubated for 16 hours at 37 C.° with unloaded (a), SHU 555A-Loaded (b) and SiMagn-Loaded erythrocytes (c) and washed with PBS. The cells fixed as reported in "Material and Methods" were stained with May-Grunwald Giemsa and observed, magnification 40×. The images show macrophage membrane interaction and phagocytosis of SiMagn-Loaded RBCs but not of SHU 555A-Loaded RBCs as compared to unloaded erythrocytes.

We estimated the final concentration of magnetic material in human erythrocytes by NMR analysis using the r1 and r2 values, obtained from calibration curve described in Materials and Methods (supra). SHU 555A incorporated into the human erythrocytes in an amount of 4.64 mM±2, when 1 ml of RBCs was dialysed with 5.6 mg Fe, and 15.2 mM±4 when the cells were dialysed with 22.4 mg Fe.

The results show that the concentration of magnetic nanoparticles encapsulated increases both with increasing amounts of the contrast agent incubated with RBCs, and with a decrease in dialysis buffer milliosmolarity, but is not influenced by the dialysis time (Table1 and Table 2). NMR measurement of $T_2*$ value of RBCs (at 44% haematocrit) loaded with Superparamagnetic nanoparticles, are lower (0.38 ms) than value of whole blood and red blood cells cleaned from serum and not dialysed (ND), at the same haematocrit (21.9 and 30 ms respectively).

TABLE 1

RESOVIST-loading experiments with different amount of agent and different dialysis times.

| Sample | Sample description | $T_1$ (msec) | $T_2$ (msec) | *[c] from r1 | **[c] from r2 |
|---|---|---|---|---|---|
| ND | Not Dialysed RBC | 2330 | 138 | / | / |
| UL | Dialysed and Unloaded RBC | 2196 | 108 | / | / |
| 50-Res-L-RBC | Dose dependence: | 355 | <5 | 1.2 mM | — |
| 100-Res-L-RBC | 500 µl of RBC70% | 104 | <5 | 4.7 mM | — |
| 200-Res-L-RBC | dialysed in presence | 46 | <5 | 10.9 mM | — |
| 400-Res-L-RBC | of different quantity of Resovist agent | 32 | <5 | 15.8 mM | — |
| 100-Res-L-RBC 75 min | Dialysis times dependence: | 92 | <5 | 5.3 mM | — |
| 100-Res-L-RBC 135 min | 500 µl of RBC70% in presence of 100 µl | 87 | <5 | 5.6 mM | — |
| 100-Res-L-RBC 195 min | Resovist agent | 81 | <5 | 6.1 mM | — |

All samples were measured at hematocrit of 44% and the paramagnetic iron content was calculated by the following formulas: *[c] = (1/T1c − 1/T1o)/r1 **[c] = (1/T2c − 1/T2o)/r2 T1o and T2o are the values of the control RBC (ND). The values indicated as <5 correspond to <5 msec and are not detectable due to instrumental sensibility.

In other words, the present inventors have discovered that only the use of SPIO in combination with a method of ensuring that the SPIO is present in the erythrocyte cytosol, rather than being adsorbed onto the cell surface, is sufficient to substantially avoid clearance of the erythrocyte and, therefore, lead to improved retention times.

The presence of nanoparticles bound on the external erythrocyte membrane is a relevant phenomena when the aim is the MRI imaging of the vascular system since this condition would activate loaded RBCs recognition by tissue macrophages as those present in the reticuloendothelial system (RES) causing their rapid elimination from blood circulation. In fact, in vitro experiments performed to test loaded RBC uptake by human macrophages shows that SHU 555A-Loaded RBC are not phagocytosed while silica mag- What is also particularly unexpected is the discovery that this value (0.38 ms) is also very significantly lower than $T_2*$ of suspensions containing the same concentration of SHU 555A agent added to whole blood (0.5 ms) or not dialysed RBCs (0.64 ms) (Table 3). Thus, the present invention permits one to obtain a T2* value lower than that determined by the presence of nanoparticles in the blood. The result of this is an improved resolution in MRI imaging.

We also evaluated the effect on T1 and T2 values of the dilution of loaded RBC samples in unprocessed blood. At the maximum dilution tested (1:250), corresponding to an injection of 20 ml of Loaded-RBC in a adult human body, the T1 values results 300 msec lower than T1 of whole blood (Table 4). Moreover T2* values of loaded RBCs (L1-RBCs)

diluted 1:125 and 1:250 in unprocessed blood are lower than value of whole blood containing not encapsulated contrast agent at the same concentration of L1-RBC at the same dilutions (14.92 versus 16.65 ms and 17.32 versus 19.79 ms, respectively) (Table 3).

Figure 3:
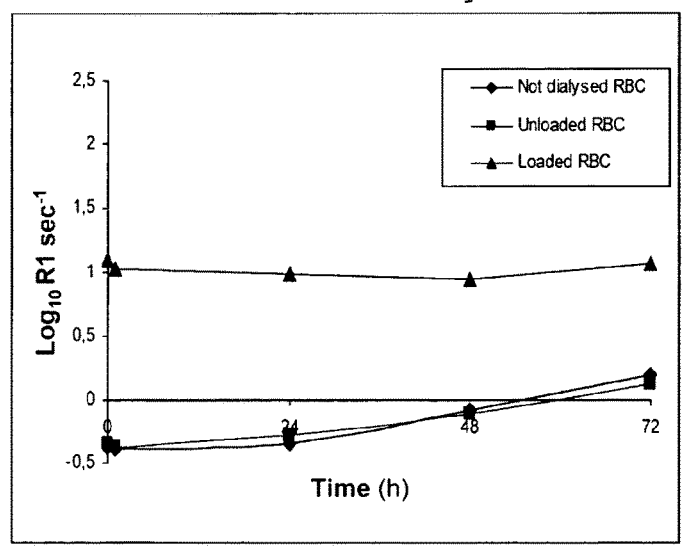
FIG. 3 is a graph illustrating in vitro stability of loaded erythrocytes incubated at 37° C. in physiological buffer and characterized by NMR measurement.

The in vitro stability of loaded erythrocytes incubated at 37° C. in physiological buffer for several times was characterised by NMR measurement (FIG. 3). The results obtained showed that T1 values in the loaded RBC remain lower respect to that of control cells for several days.

TABLE 2

RESOVIST-loading experiments with dialysis buffer with different milliosmolalities. The values indicated as <5 are not significant due to instrumental sensibility.

| Sample | Sample Description | $T_1$ (msec) | $T_2$ (msec) | [c] from r1 | [c] from r2 |
|---|---|---|---|---|---|
| ND | Not dialysed RBC | 2289 | 149.4 | / | / |
| Res-L-RBC (300mOsm) | Not dialysed RBC incubated with Resovist | 1274 | 18.6 | 0.13 mM | 0.31 mM |
| Res-L-RBC (64mOsm) | 500 µl of RBC70% dialysed in presence of 100 µl Resovist agent against dialysis buffer at different milliosmolarity | 75 | <5 | 6.6 mM | — |
| Res-L-RBC (110mOsm) | | 104 | <5 | 4.7 mM | — |
| Res-L-RBC (165mOsm) | | 656 | 12.4 | 0.44 mM | 0.48 mM |
| Res-L-RBC (212mOsm) | | 800 | 13.2 | 0.33 mM | 0.44 mM |

TABLE 3

NMR measurement of T1, T2 and T2* values of loaded RBCs.

| Sample | Sample description | $T_1$ (msec) | $T_2$ (msec) | $T_2^*$ (msec) |
|---|---|---|---|---|
| Control | Whole blood | | | 21.96 |
| ND | Not dialysed RBC | 2294 | 140.2 | 30 |
| L1-RBCs | 500 µl of RBC70% dialysed in presence of 100 µl Resovist agent | 142.5 | 2.27 | 0.38 |
| ND + res | Resovist agent added to not dialyzed RBC at the same concentration of L1- | 123.1 | 3.37 | 0.64 |
| W.B. + res | Resovist agent added to whole blood at the same concentration of L1-RBCs | 129.6 | 6.9 | 0.5 |
| L1-RBC (1:125) | Loaded RBC diluted with whole blood | 1777 | 68.3 | 14.92 |
| L1-RBC (1:250) | | 1894 | 86.58 | 17.32 |
| W.B + res (1:125) | W.B + res diluted with whole blood | 1713 | 61.7 | 16.65 |
| W.B + res (1:250) | | 1845 | 80.6 | 19.79 |

Figure 4:
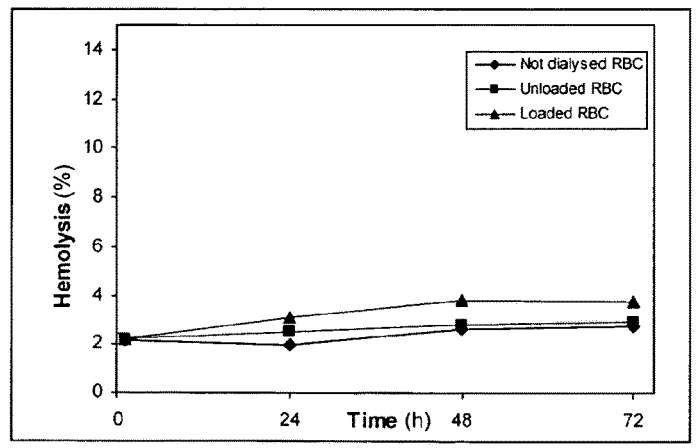
FIG. 4 is a graph illustrating in vitro release of haemoglobin from loaded cells with respect to control cells.

It is noteworthy that no significant amount of haemoglobin is released from loaded cells with respect to control cells (loaded 3.7% versus 2.7% of control cells not dialysed—FIG. 4).

The same loading procedure was applied to murine erythrocytes obtaining an encapsulation of Resovist corresponding to a concentration of paramagnetic iron ranging from 1.5 mM to 3.75 mM (for 500 µl of RBC treated with 100 µl of Resovist), Table 5.

TABLE 5

In vivo pharmacokinetic NMR results after intraperitoneal injection of 100-res-loaded erythrocytes in balb mice.

| Samples | $T_1$ (msec) | $T_2$ (msec) | % Ht | [c] |
|---|---|---|---|---|
| ND | 2300 | 134 | 44 | / |
| *100-Res-L-RBC | 246 | <5 | 44 | 1.5 mM |
| ND | 3411 | 401.7 | 10 | / |
| 100-Res-L-RBC (peritoneal injected) | 894 | <5 | 10 | 0.3 mM |

*500 µl of RBC 70% are dialysed for 75 min in the presence of 100 µl (2.8 mg Fe) Resovist agent

TABLE 4

NMR measurement of SHU555A (Resovist) in Human Loaded Erythrocytes (5.6 mg Fe/ml RBC 70%) diluted with whole blood. The values indicated as <5 are not significant due to instrumental sensibility.

| Sample | Sample description | $T_1$ (msec) | $T_2$ (msec) | [c] from r1 | [c] from r2 | [c] diluition estimated |
|---|---|---|---|---|---|---|
| Control | Whole blood | 2130 | 116.4 | / | / | / |
| Unloaded | Dialyzed RBC | 2114 | 105.6 | / | / | / |
| Ln.a. | Res-loaded RBC not magnetically | 81 | <5 | 6.1 mM | — | — |
| Ln.a 1:2 | RBC-loaded diluted with whole blood | 134 | <5 | 3.6 mM | — | 3.05 mM |
| Ln.a 1:50 | | 1309 | 38.6 | 0.118 mM | 0.113 | 0.122 mM |
| Ln.a 1:100 | | 1582 | 59.0 | 0.065 mM | 0.054 | 0.061 mM |
| Ln.a 1:200 | | 1714 | 71.2 | 0.045 mM | 0.036 | 0.030 mM |
| Ln.a 1:250 | | 1790 | 79.8 | 0.036 mM | 0.026 | 0.024 mM |

The in vivo experiments on Balb/C mice were performed to investigated the presence of magnetic nanoparticle-loaded RBC in the vascular system and blood withdrawal samples were evaluated by NMR analysis during long intervals of time (days).

Figure 5:
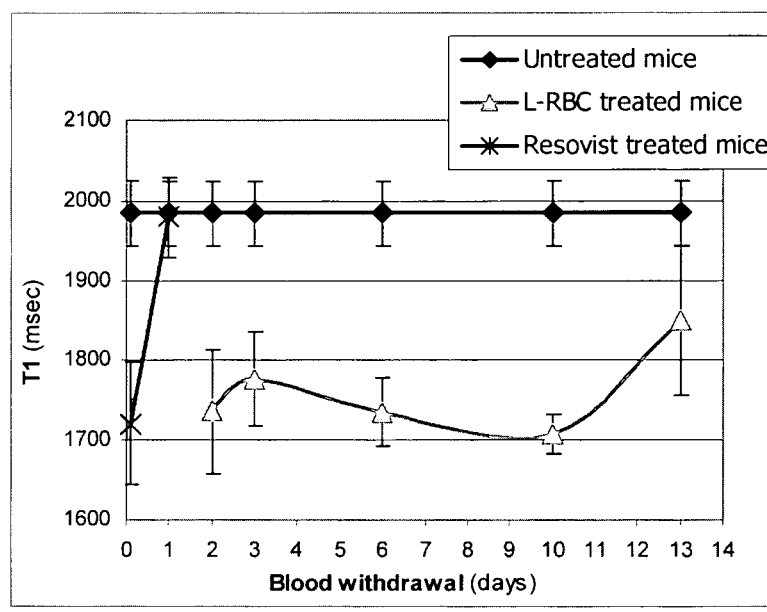
FIG. 5 is a graph illustrating the biologic half-life of magnetic nanoparticles in untreated mice, L-RBC treated mice and RESOVIST treated mice.

The results reported in FIG. 5 show that the biologic half-life of magnetic nanoparticles within the loaded RBC fraction of whole blood was similar to the half-life of unprocessed murine erythrocytes (12 days), while injection in mice of an equivalent amount of free Resovist suspension produce a measurable T1 only for few hours and totally disappeared from circulation within 24 hours.

REFERENCES

Allkemper T., Bremer C., Matuszewski L., Ebert W., Reimer P.; 2002. Contrast-enhanced Blood-Pool MR angiography with optimized iron oxides: effect of size and dose on vascular contrast enhancement in rabbits. *Radiology* 223 (2): 432-438.

Araujo L., Lobenberg R., Kreuter J.; 1999. Influence of the surfactant concentration on the body distribution of nanoparticles. *Journal of colloid and interface science* 212: 474-482.

Babincova M., Sourivong P., Leszczynska D., Babinec P.; 2000. Blood-specific whole-body electromagnetic hyperthermia. *Medical Hypotheses* 55(6): 459-460.

Bacri J., Perzynski R., Salin D., Cabuil V., Massart R.; 1990. Ionic ferrofluids: A crossing of chemistry and physics. *Journal of Magnetism and Magnetic Materials* 85, 27.

Berry C. C., Curtis A. S. G.; 2003. Functionalisation of magnetic nanoparticles for applications in biomedicine. *J. Phys. D: Appl. Phys.* 36: 198-206.

Bonnemain B.; 1995. Superparamagnetic agents: physicochemical characteristics and preclinical imaging evaluation for potential applications in: Contrast Media Research (CMR). *Naantali* 17-22: 35.

Bonnemain B.; 1998. Superparamagnetic agents in magnetic resonance imaging: physicochemical characteristics and clinical applications a review. *Journal of Drug Targeting* 6(3): 167-174.

Brähler M., Georgieva R., Buske N., Müller A., Müller S., Pinkernelle J., Teichgräber U., Voigt A., Bäumler H.; 2006. Magnetite-loaded carrier erythrocytes as contrast agents for magnetic resonance imaging. *Nano Letters* 6(11): 2505-2509.

Brigger I., Dubernet C., Couvreur P.; 2002. Nanoparticles in cancer therapy and diagnosis. *Adv. Drug Deliv. Rev.* 54, 631-651.

Cornell R. M., Schertmann U.; 1991. Iron oxides in the laboratory; preparation and characterization. *VCH Publishers*, Weinheim.

Davis S. S.; 1997. Biomedical applications of nanotechnology-implications for drug targeting and gene therapy. *Trends Biotechnol.* 15: 217-224.

Frank H., Weissleder R., Brady T. J.; Enhancement of MR angiography with iron oxide: preliminary studies in whole-blood phantom and in animal. *AJR Am J Roentgenol* 162: 209-213.

Gaur U., Sahoo S. K., De T. K., Ghosh P. C., Maitra A., Ghosh P. K.; 2000. Biodistribution of fluoresceinated dextran using novel nanoparticles evading reticuloendothelial system. *Int. J. Pharm.* 202: 1-10.

Halavaara J., Tervahartiala P., Isonieme H., Hockerstedt K.; 2002. Efficacy of sequential use of superparamagnetic iron oxide and gadolinium in liver MR imaging. *Acta radiologica* 43: 180-185.

Hilger I., Fruhauf K., Andra W., Hiergeist R., Hergt R., Kaiser W. A.; 2002. Heating potential of iron oxides for therapeutic purposes in interventional radiology. *Acad. Radiol.* 9: 198-202.

Ito A., Shinkai M., Honda H., Kobayashi T.; 2005. Medical Application of Functionalized Magnetic Nanoparticles. *Journal of Bioscience and Bioengineerin;* 100(1): 1-11.

Jain S. K., Vyas S. P.; 1994. Magnetically responsive diclofenac sodium-loaded erythrocytes: Preparation and in vitro characterization. *J. Microencapsulation* 11(2): 141-151.

Johnson K. M., Tao J. Z., Kennan R. P., Gore J. C.; 1998. Gadolinium-bearing red cells as blood pool MRI contrast agents. *Magn. Reson. Med.* 40(1): 133-142.

Jung C. W., Jacobs P.; 1995. Physical and chemical properties of superparamagnetic iron oxide MR contrast agents: ferumoxides, ferumoxtran, ferumoxsil. *Magnetic Resonance Imaging* 13(5): 661-674.

Kreuter J. 1994. Drug targeting with nanoparticles. *Eur. J. Drug. Metab. Pharmacokinet* 19: 253-256.

Kubaska S., Sahani D. V., Saini S., Hahn P. F., Halpern E.; 2001. Dual contrast enhanced magnetic resonance imaging of the liver with superparamagnetic iron oxide followed by gadolinium for lesion detection and characterization. *Clin. Radiol.* 56: 410-415.

Low R. N.; 1997. Contrast agents for MR imaging of the liver. J. Magn. Reson. Imaging 7(1): 56-67.

Lübbe A. S., Alexiou C., Bergemann C.; 2001. Clinical applications of magnetic drug targeting. *J. Surg. Res.* 95:200, 206.

Magnani M., Rossi L., Fraternale A., Bianchi M., Antonelli A., Crinelli R., Chiarantini L.; 2002. Erythrocyte-mediated delivery of drug, peptides and modified oligonucleotides. *Gene Ther.* 9(11): 749-751.

Moghimi S. M., Hunter A. C., Murray J. C.; 2001. Long-circulating and target specific nanoparticles: theory to practise. *Pharm. Rev.* 53: 283-318.

Morais P. C., Santos J. G., Silveira L. B., Gansau C., Buske N., Nunes W. C., Sinnecker J. P.; 2004. Susceptibility investigation of the nanoparticle coating-layer effect on the particle interaction in biocompatible magnetic fluids. *Journal of Magnetism and Magnetic Materials* 272-276: 2328-2329.

Petri-Fink A., Chastellain M., Juillerat-Jeanneret A. Ferrari A., Hofmann H., 2005. Development of functionalized magnetic nanoparticles for interaction with human cancer cells. *Biomaterials* 26: 2685-2694.

Reimer P., Tombach B.; 1998. Hepatic MRI with SPIO: detection and characterization of focal liver lesions. *Eur. Radiol.* 8: 1198-1204.

Sudimack J., Lee R. J.; 2000. Targeted drug delivery via the folate receptor. *Adv. Drug Del. Rev.* 41: 147-162.

Vyas S. P., Jain S. K.; 1994. Preparation and in vitro charactezization of a magnetically responsive ibuprofen-loaded erythrocytes carrier. *Microencapsulation* 11(1): 19-29.

Wang Yi-X. J., Hussain S. M., Krestin G. P.; 2001. Superparamagnetic iron oxide contrast agents: physicochemical characteristics and applications in MR imaging. *Eur. Radiol.* 11: 2319-2331.

Wilhelm C., Billotey C., Roger J., Pons J. N., Bacri J. C., Gazeau F.; 2003. Intracellular uptake of anionic superparamagnetic nanoparticles as a function of their surface coating. *Biomaterials* 24: 1001-1011.

Zhou J., Leuschner C., Kumar C., Hormes J. F., Soboyejo W. O.; 2006. Sub-cellular accumulation of magnetic nanoparticles in breast.

The invention claimed is:

1. A method for magnetic resonance imaging, said method comprising:
   administering a preparation comprising a plurality of erythrocytes to a subject in need thereof, and thereafter subjecting said subject to magnetic resonance imaging,
   wherein the plurality of erythrocytes comprises viable erythrocytes that contain superparamagnetic nanoparticulate iron oxide (SPIO),
   wherein the SPIO is substantially encapsulated within the cytosol of the erythrocytes such that the erythrocytes are not recognized by macrophages unless they are at the end of their physiological life,
   wherein the amount of SPIO present in the preparation is sufficient that the preparation is useful as a magnetic resonance imaging contrast agent,
   wherein the erythrocytes that contain superparamagnetic nanoparticulate iron oxide are viable in vivo having a half-life similar to the half-life of native erythrocytes, and
   wherein the SPIO is coated with carboxydextran.

2. A method according to claim 1, wherein the amount of SPIO in the erythrocytes is between about 1 mM and 40 mM.

3. A method according to claim 1, wherein the average total particle size of the SPIO is no greater than 80-90 nm.

4. A method according to claim 1, wherein the erythrocytes comprise one or more drugs.

5. A method according to claim 4, wherein the drug is selected from the group consisting of: anti-inflammatory drugs, immunosuppressive drugs, antiviral drugs, antiretroviral drugs, anticancer drugs, oligonucleotides, monoclonal antibodies, peptides, peptide nucleic acids, photosensitizing drugs, infra red fluorescent agents, and mixtures of any two or more thereof.

6. A method according to claim 1, wherein the SPIO has the general formula $Fe_2^{3+}O_3M^{2+}O$ where $M^{2+}$ is a divalent metal cation.

7. A method according to claim 6, wherein the SPIO is magnetite ($M^{2+}$ is ferrous iron).

8. A method according to claim 6, wherein $M^{2+}$ is selected from the group consisting of: ferrous iron, manganese, nickel, cobalt, and magnesium.

9. A method for the treatment of a condition wherein the erythrocytes are localisable by external magnetic force in the vicinity of an area to be treated, said method comprising:
   administering a preparation comprising a plurality of erythrocytes to a subject in need thereof, and thereafter exposing said subject to an external magnetic force in the vicinity of the area to be treated,
   wherein the plurality of erythrocytes comprises viable erythrocytes that contain superparamagnetic nanoparticulate iron oxide (SPIO),
   wherein the SPIO is substantially encapsulated within the cytosol of the erythrocytes such the erythrocytes are not recognized by macrophages unless they are at the end of their physiological life,
   wherein the amount of SPIO present in the preparation is sufficient that the preparation is useful as a magnetic resonance imaging contrast agent,
   wherein the erythrocytes that contain superparamagnetic nanoparticulate iron oxide are viable in vivo having a half-life similar to the half-life of native erythrocytes, and
   wherein the SPIO is coated with carboxydextran.

10. A method of resonance imaging, comprising:
    administering viable erythrocytes that contain superparamagnetic nanoparticulate iron oxide (SPIO) to a subject in need thereof, and thereafter subjecting said subject to magnetic resonance imaging,
    wherein the SPIO is substantially encapsulated within the cytosol of the erythrocytes such that the erythrocytes are not recognized by macrophages unless they are at the end of their physiological life,
    wherein the erythrocytes that contain superparamagnetic nanoparticulate iron oxide are viable in vivo having a half-life similar to the half-life of native erythrocytes, and
    wherein the SPIO is coated with carboxydextran.

11. A method according to claim 10, wherein erythrocytes are:
    removed from a patient,
    separated from other blood cells,
    loaded with SPIO to produce viable erythrocytes containing SPIO,
    wherein the SPIO is substantially encapsulated within the cytosol of the erythrocytes such that the erythrocytes are not recognized by macrophages unless they are at the end of their physiological life,
    the loaded erythrocytes are thereafter reintroduced into the patient, and
    wherein the erythrocytes that contain superparamagnetic nanoparticulate iron oxide are viable in vivo having a half-life similar to the half-life of native erythrocytes.

12. A method according to claim 10, wherein the amount of SPIO in the erythrocytes is between about 1 mM and 40 mM.

13. A method according to claim 10, wherein the average total particle size of the SPIO is no greater than 80-90 nm.

14. A method according to claim 10, wherein the erythrocytes comprise one or more drugs.

15. A method according to claim 14, wherein the drug is selected from the group consisting of: anti-inflammatory drugs, immunosuppressive drugs, antiviral drugs, antiretroviral drugs, anticancer drugs, oligonucleotides, monoclonal antibodies, peptides, peptide nucleic acids, photosensitizing drugs, infrared fluorescent agents, and mixtures of any two or more thereof.

16. A method according to claim 10, wherein the SPIO has the general formula $Fe_2^{3+}O_3M^{2+}O$ where $M^{2+}$ is a divalent metal cation.

17. A method according to claim 16, wherein the SPIO is magnetite ($M^{2+}$ is ferrous iron).

18. A method according to claim 16, wherein $M^{2+}$ is selected from the group consisting of: ferrous iron, manganese, nickel, cobalt, and magnesium.

19. A method of increasing the resonance imaging resolution of superparamagnetic iron oxide, comprising:
    substantially encapsulating said superparamagnetic iron oxide within the cytosol of the erythrocytes as to produce viable erythrocytes that are not recognizable by macrophages unless they are at the end of their physiological life, and
    resonance imaging said erythrocytes in vivo,
    wherein the erythrocytes that contain superparamagnetic nanoparticulate iron oxide are viable in vivo having a half-life similar to the half-life of native erythrocytes, and
    wherein the SPIO is coated with carboxydextran.

20. A method for magnetic resonance imaging, said method comprising:
    administering a preparation comprising a plurality of erythrocytes to a subject in need thereof, and thereafter subjecting said subject to magnetic resonance imaging,
    wherein the plurality of erythrocytes comprises viable erythrocytes that contain monodispersed superparamagnetic nanoparticulate iron oxide (SPIO), wherein the SPIO is substantially encapsulated within the cytosol of the erythrocytes by dialysing a preparation of said erythrocytes against a hypotonic buffer having an osmolarity of between 60 and 120 mOsm,
   wherein the amount of SPIO present in the preparation is sufficient that the preparation is useful as a magnetic resonance imaging contrast agent, and
   wherein the SPIO is coated with carboxydextran.

* * * * *